(12) United States Patent
Müller et al.

(10) Patent No.: US 6,172,063 B1
(45) Date of Patent: Jan. 9, 2001

(54) FUNGICIDAL MIXTURES

(75) Inventors: Bernd Müller, Frankenthal; Hubert Sauter, Mannheim; Eberhard Ammermann, Heppenheim; Gisela Lorenz, Hambach; Siegfried Strathmann, Limburgerhof; Maria Scherer, Landau; Klaus Schelberger, Gönnheim; Joachim Leyendecker, Ladenburg, all of (DE)

(73) Assignee: BASF Aktiengesellschaft, Ludwigshafen (DE)

( * ) Notice: Under 35 U.S.C. 154(b), the term of this patent shall be extended for 0 days.

(21) Appl. No.: 09/180,295

(22) PCT Filed: Apr. 25, 1997

(86) PCT No.: PCT/EP97/02128

§ 371 Date: Nov. 5, 1998

§ 102(e) Date: Nov. 5, 1998

(87) PCT Pub. No.: WO97/42821

PCT Pub. Date: Nov. 20, 1997

(30) Foreign Application Priority Data

May 9, 1996 (DE) .............................................. 196 18 680

(51) Int. Cl.[7] ........................ A61K 31/535; A01N 37/18; A01N 43/56; A01N 43/64

(52) U.S. Cl. ...................... 514/237.5; 514/383; 514/407; 514/622

(58) Field of Search ................................... 514/383, 407, 514/237.5, 622

(56) References Cited

FOREIGN PATENT DOCUMENTS

| 120 321 | 10/1984 | (EP) . |
| 648 416 | 4/1995 | (EP) . |
| 96/01256 | 1/1996 | (WO) . |
| 96/01258 | 1/1996 | (WO) . |

OTHER PUBLICATIONS

Tomlin, The Pesticide Manual Incorporating The Agrochemicals Handbook, 10th Ed. (1995) pp. 351–352.*
Agrow, Nov. 3rd, 1995, No. 243.

* cited by examiner

Primary Examiner—Allen J. Robinson

(74) Attorney, Agent, or Firm—Keil & Weinkauf

(57) ABSTRACT

A fungicidal mixture containing
  a) a carbamate of the formula I,

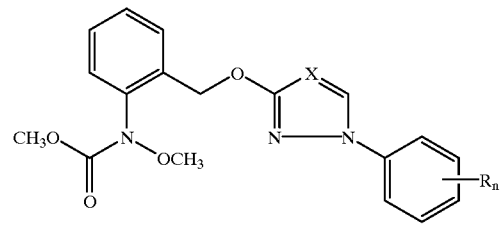

where X is CH or N, n is 0, 1 or 2 and R is halogen, $C_1$–$C_4$-alkyl or $C_1$–$C_4$-haloalkyl, it being possible for the radicals R to be different if n is 2, and
  b) a carboxamide II selected from the group consisting of the compounds IIa and IIb

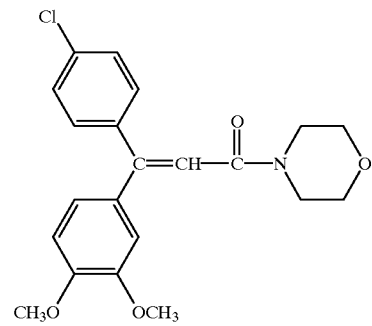

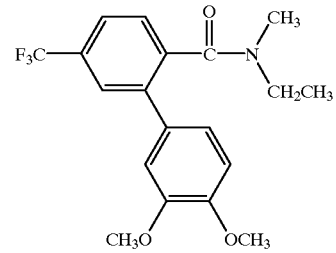

in a synergistically active amount is described.

16 Claims, No Drawings

FUNGICIDAL MIXTURES

This application is a 371 of PCT/EP97/02128, filed Apr. 25, 1997.

The present invention relates to a fungicidal mixture which contains a) a carbamate of the formula I,

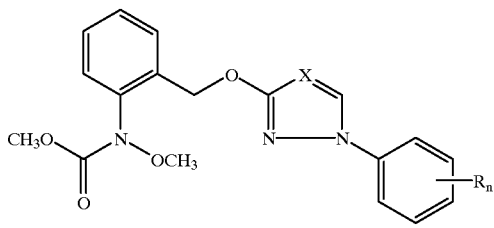

where X is CH or N, n is 0, 1 or 2 and R is halogen, $C_1$–$C_4$-alkyl or $C_1$–$C_4$-haloalkyl, it being possible for the radicals R to be different if n is 2, and b) a carboxamide II selected from the group consisting of the compounds IIa and IIb

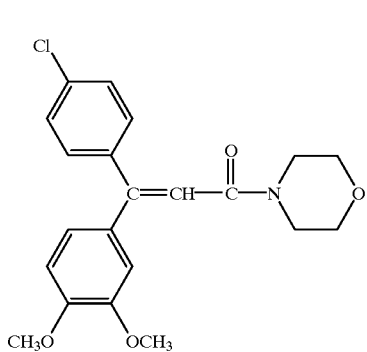

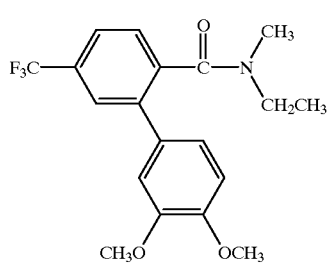

in a synergistically active amount.

The invention additionally relates to methods of controlling harmful fungi using mixtures of the compounds I and II and the use of the compound I and of the compound II for the production of mixtures of this type.

The compounds of the formula I, their preparation and their action against harmful fungi are known from the literature (WO-A 96/01,256 and 96/01,258).

Likewise known are the carboxamides II [IIa: common name: dimethomorph, EP-A 120 321; IIb: proposed common name: flumetover, AGROW No. 243 (1995) 22], their preparation and their action against harmful fungi.

With a view to lowering the application rates and improving the spectrum of action of the known compounds, it is an object of the present invention to provide mixtures which, together with a decreased total amount of active compounds applied, have an improved action against harmful fungi (synergistic mixtures).

We have found that this object is achieved by the mixtures defined at the outset. We have additionally found that on simultaneous joint or separate application of the compounds I and the compounds II or on application of the compounds I and the compounds II in succession harmful fungi can be controlled better than with the individual compounds.

The formula I in particular represents carbamates where the combination of the substituents corresponds to one line of the following table:

| No. | X | $R_n$ |
|---|---|---|
| I.1 | N | 2-F |
| I.2 | N | 3-F |
| I.3 | N | 4-F |
| I.4 | N | 2-Cl |
| I.5 | N | 3-Cl |
| I.6 | N | 4-Cl |
| I.7 | N | 2-Br |
| I.8 | N | 3-Br |
| I.9 | N | 4-Br |
| I.10 | N | 2-$CH_3$ |
| I.11 | N | 3-$CH_3$ |
| I.12 | N | 4-$CH_3$ |
| I.13 | N | 2-$CH_2CH_3$ |
| I.14 | N | 3-$CH_2CH_3$ |
| I.15 | N | 4-$CH_2CH_3$ |
| I.16 | N | 2-$CH(CH_3)_2$ |
| I.17 | N | 3-$CH(CH_3)_2$ |
| I.18 | N | 4-$CH(CH_3)_2$ |
| I.19 | N | 2-$CF_3$ |
| I.20 | N | 3-$CF_3$ |
| I.21 | N | 4-$CF_3$ |
| I.22 | N | 2,4-$F_2$ |
| I.23 | N | 2,4-$Cl_2$ |
| I.24 | N | 3,4-$Cl_2$ |
| I.25 | N | 2-Cl, 4-$CH_3$ |
| I.26 | N | 3-Cl, 4-$CH_3$ |
| I.27 | CH | 2-F |
| I.28 | CH | 3-F |
| I.29 | CH | 4-F |
| I.30 | CH | 2-Cl |
| I.31 | CH | 3-Cl |
| I.32 | CH | 4-Cl |
| I.33 | CH | 2-Br |
| I.34 | CH | 3-Br |
| I.35 | CH | 4-Br |
| I.36 | CH | 2-$CH_3$ |
| I.37 | CH | 3-$CH_3$ |
| I.38 | CH | 4-$CH_3$ |
| I.39 | CH | 2-$CH_2CH_3$ |
| I.40 | CH | 3-$CH_2CH_3$ |
| I.41 | CH | 4-$CH_2CH_3$ |
| I.42 | CH | 2-$CH(CH_3)_2$ |
| I.43 | CH | 3-$CH(CH_3)_2$ |
| I.44 | CH | 4-$CH(CH_3)_2$ |
| I.45 | CH | 2-$CF_3$ |
| I.46 | CH | 3-$CF_3$ |
| I.47 | CH | 4-$CF_3$ |
| I.48 | CH | 2,4-$F_2$ |
| I.49 | CH | 2,4-$Cl_2$ |
| I.50 | CH | 3,4-$Cl_2$ |
| I.51 | CH | 2-Cl, 4-$CH_3$ |
| I.52 | CH | 3-Cl, 4-$CH_3$ |

The compounds I.12, I.23, I.32 and I.38 are particularly preferred.

Because of the basic character, the compounds I and II are able to form salts or adducts with inorganic or organic acids or with metal ions.

Examples of inorganic acids are hydrohalic acids such as hydrofluoric acid, hydrochloric acid, hydrobromic acid and hydriodic acid, sulfuric acid, phosphoric acid and nitric acid.

Suitable organic acids are, for example, formic acid, carbonic acid and alkanoic acids such as acetic acid, trifluoroacetic acid, trichloroacetic acid and propionic acid as well as glycolic acid, thiocyanic acid, lactic acid, succinic acid, citric acid, benzoic acid, cinnamic acid, oxalic acid, alkylsulfonic acids (sulfonic acids having straight-chain or branched alkyl radicals having from 1 to 20 carbon atoms), arylsulfonic acids or -disulfonic acids (aromatic radicals such as phenyl and naphthyl which carry one or two sulfonic acid groups), alkylphosphonic acids (phosphonic acids having straight-chain or branched alkyl radicals having from 1 to 20 carbon atoms), arylphosphonic acids or -diphosphonic acids (aromatic radicals such as phenyl and naphthyl which carry one or two phosphoric acid radicals), it being possible for the alkyl and aryl radicals to carry further substituents, e.g. p-toluenesulfonic acid, salicylic acid, p-aminosalicylic acid, 2-phenoxybenzoic acid, 2-acetoxybenzoic acid, etc.

Suitable metal ions are in particular the ions of the elements of the second main group, in particular calcium and magnesium, the third and fourth main group, in particular aluminum, tin and lead, and of the first to eighth subgroup, in particular chromium, manganese, iron, cobalt, nickel, copper, zinc and others. The metal ions of the elements of the subgroups of the fourth period are particularly preferred. The metals can be present here in the various valences befitting them.

Preferably, in the preparation of the mixtures the pure active compounds I and II are employed, with which, if required, further compounds active against harmful fungi or other pests such as insects, arachnids or nematodes, or alternatively herbicidal or growth-regulating active compounds or fertilizers, can be admixed.

The mixtures of the compounds I and II and the simultaneous joint or separate use of the compounds I and II are distinguished by an outstanding action against a wide spectrum of phytopathogenic fungi, in particular of the Ascomycetes, Deuteromycetes, Phycomycetes and Basidiomycetes classes. In some cases they are systemically active and can therefore also be employed as foliar and soil fungicides.

They are of particular importance for controlling a multiplicity of fungi on various crop plants such as cotton, vegetable plants (e.g. cucumbers, beans and cucurbits), barley, grass, oats, coffee, corn, fruit plants, rice, rye, soybeans, grapes, wheat, decorative plants, sugar cane and a multiplicity of seeds.

They are particularly suitable for controlling the following phytopathogenic fungi: *Erysiphe graminis* (powdery mildew) on cereals, *Erysiphe cichoracearum* and *Sphaerotheca fuliginea* on cucurbits, *Podosphaera leucotricha* on apples, *Uncinula necator* on vines, Puccinia species on cereals, Rhizoctonia species on cotton, rice and lawns, Ustilago species on cereals and sugar cane, *Venturia inaequalis* (scab) on apples, Helminthosporium species on cereals, Rhynosporium Secalis, *Septoria nodorum* on wheat, *Botrytis cinerea* (gray mold) on strawberries, vegetables, decorative plants and vines, *Cercospora arachidicola* on ground-nuts, *Pseudocercosporella herpotrichoides* on wheat and barley, *Pyricularia oryzae* on rice, *Phytophthora infestans* on potatoes and tomatoes, *Plasmopara viticola* on vines, Alternaria species on vegetables and fruit, and Fusarium and Verticillium species.

They are additionally utilizable in the protection of materials (e.g. wood preservation), for example against *Paecilomyces variotii*.

The compounds I and II can be applied together or separately at the same time or in succession, the sequence in the case of separate application in general having no effect on the control success.

The compounds I and II are customarily applied in a weight ratio of from 20:1 to 0.1:2, preferably 10:1 to 0.2:1, in particular 5:1 to 0.5:1.

Depending on the type of effect desired, the application rates in the mixtures according to the invention for the compounds I are from 0.01 to 0.5 kg/ha, preferably 0.05 to 0.5 kg/ha, in particular 0.05 to 0.3 kg/ha.

The application rates for the compounds II are correspondingly from 0.05 to 1 kg/ha, preferably 0.1 to 1 kg/ha, in particular 0.1 to 0.8 kg/ha.

In the treatment of seed, in general application rates of mixture of from 0.001 to 50 g/kg of seed, preferably 0.01 to 10 g/kg, in particular 0.01 to 5 g/kg, are used.

If harmful fungi which are pathogenic to plants are to be controlled, the separate or joint application of the compounds I and II or the mixtures of the compounds I and II is carried out by spraying or dusting the seeds, the plants or the soils before or after sowing the plants or before or after the emergence of the plants.

The fungicidal synergistic mixtures or the compounds I and II according to the invention can be prepared, for example, in the form of directly sprayable solutions, powders and suspensions or in the form of high-percentage aqueous, oily or other suspensions, dispersions, emulsions, oil dispersions, pastes, dusting compositions, broadcasting compositions or granules and applied by spraying, atomizing, dusting, broadcasting or watering. The application form is dependent on the intended use; it should in any case guarantee a distribution of the mixture according to the invention which is as fine and uniform as possible.

The formulations are prepared in a manner known per se, e.g. by adding solvents and/or carriers. Inert additives such as emulsifiers or dispersants are customarily admixed with the formulations.

Suitable surface-active substances are the alkali metal, alkaline earth metal or ammonium salts of aromatic sulfonic acids, e.g. lignosulfonic, phenolsulfonic, naphthalenesulfonic and dibutylnaphthalenesulfonic acid, and also of fatty acids, alkyl- and alkylarylsulfonates, alkyl, lauryl ether and fatty alcohol sulfates, as well as salts of sulfated hexa-, hepta- and octadecanols or fatty alcohol glycol ethers, condensation products of sulfonated naphthalene and its derivatives with formaldehyde, condensation products of naphthalene or of the naphthalenesulfonic acids with phenol and formaldehyde, polyoxyethylene octylphenyl ether, ethoxylated isooctyl-, octyl- or nonylphenol, alkylphenyl or tributylphenyl polyglycol ethers, alkylaryl polyether alcohols, isotridecyl alcohol, fatty alcohol-ethylene oxide condensates, ethoxylated castor oil, polyoxyethylene or polyoxypropylene alkyl ethers, lauryl alcohol polyglycol ether acetate, sorbitol esters, lignin-sulfite waste liquors or methylcellulose.

Powder, broadcasting and dusting compositions can be prepared by mixing or joint grinding of the compounds I or II or the mixture of the compounds I and II with a solid carrier.

Granules (e.g. coated, impregnated or homogeneous granules) are customarily prepared by binding the active compound or the active compounds to a solid carrier.

Fillers or solid carriers used are, for example, mineral earths such as silica gel, silicic acids, silicates, talc, kaolin, limestone, lime, chalk, bole, loess, clay, dolomite, diatomaceous earth, calcium and magnesium sulfate, magnesium oxide, ground synthetic materials, and also fertilizers such as ammonium sulfate, ammonium phosphate, ammonium nitrate, ureas and vegetable products such as cereal flour, tree bark, wood and nutshell meal, cellulose powder or other solid carriers.

The formulations in general contain from 0.1 to 95% by weight, preferably 0.5 to 90% by weight, of one of the compounds I or II or of the mixture of the compounds I and II. The active compounds are employed here in a purity of from 90% to 100%, preferably 95% to 100% (according to NMR spectrum or HPLC.

The compounds I or II or the mixtures or the corresponding formulations are applied by treating the harmful fungi or the plants, seeds, soil, surfaces, materials or spaces to be kept free from them with a fungicidally active amount of the mixture, or of the compounds I and II in the case of separate application. Application can be carried out before or after attack by the harmful fungi.

It is possible to show the fungicidal action of the compounds and of the mixtures by the following tests:

The active compounds are prepared separately or together as a 10% strength emulsion in a mixture of 70% by weight of cyclohexanone, 20% by weight of Nekanil® LN (Lutensol® AP6, wetting agent having emulsifier and dispersant action based on ethoxylated alkylphenols) and 10% by weight of Emulphor® EL (Emulan® EL, emulsifier based on ethoxylated fatty alcohols) and accordingly diluted to the desired concentration with water.

Evaluation is carried out by determining the attacked leaf areas in percent. These percentage values are converted into efficiencies. The efficiencies to be expected of the active compound mixtures were determined by the Colby formula [R. S. Colby, Weeds 15 (1967), 20–22] and compared with the observed efficiencies.

Colby formula:

$$E = x+y-xxy/100$$

E efficiency to be expected, expressed in % of the untreated control, on use of the mixture of the active compounds A and B in the concentrations a and b x the efficiency, expressed in % of the untreated control, on use of the active compound A in the concentration a y the efficiency, expressed in % of the untreated control, on use of the active compound B in the concentration b The efficiency (W) is calculated according to the formula of Abbot as follows:

$$W = (1-\alpha) \times 100/\beta$$

α corresponds to the fungal attack on the treated plants in % and

β corresponds to the fungal attack on the treated (control) plants in %

In the case of an efficiency of 0, the attack on the treated plants corresponds to that on the untreated control plants; in the case of an efficiency of 100, the treated plants exhibit no attack.

EXAMPLES 1–9

Activity against *Phytophthora infestans* on tomatoes

Leaves of potted plants of the variety "Große Fleischtomate" were sprayed until dripping wet with an aqueous suspension which was prepared from a stock solution of 10% active compound, 63% cyclohexanone and 27% emulsifier. On the following day, the leaves were infected with an aqueous zoospore suspension of *Phytophthora infestans*. The plants were then placed in a water vapor-saturated chamber at from 16 to 18° C. After 6 days, the blight on the untreated, but infected control plants had developed so severely that it was possible to determine the attack visually in %.

The visually determined values for the percentage of affected fruit slices were converted in efficiencies as % of the untreated control. Efficiency 100 is 0% attack. The efficiencies to be expected for active compound combinations were determined according to the Colby formula (Colby, S. R. (Calculating synergistic and antagonistic responses of herbicide Combinations", Weeds, 15, pp. 20–22, 1967) and compared with the observed efficiencies.

TABLE 2

| Ex. | Active compound | Active compound concentration in the spray liquor in ppm | Efficiency in % of the untreated control |
|---|---|---|---|
| 1v | Control (untreated) | (100% attack) | 0 |
| 2v | Compound No. I.32 from Tab. 1 = A | 0.31 | 90 |
| 3v | Compound No. I.38 Tab. 2 = B | 0.31 | 70 |
| 4v | IIa = Dimethomorph | 0.31 | 0 |
| 5v | IIb = Flumetover | 0.31 | 0 |

TABLE 3

| Ex. | Active compound content in the spray liquor in ppm | Observed efficiency | Calculated efficiency *) |
|---|---|---|---|
| 6 | 0.31A + 0.31IIa | 98 | 90 |
| 7 | 0.31A + 0.31IIb | 98 | 90 |
| 8 | 0.31B + 0.31IIa | 90 | 70 |
| 9 | 0.31B + 0.31IIb | 95 | 70 |

*) calculated according to the Colby formula

From the results of the experiments it emerges that the observed efficiency at all mixing ratios is higher than the efficiency precalculated according to the Colby formula.

EXAMPLES 10–22

Activity against *Plasmopara viticola*

Leaves of potted vines of the variety "Müller-Thurgau" were sprayed until dripping wet with aqueous active compound preparation which was prepared using a stock solution of 10% active compound, 65% cyclohexanone and 27% emulsifier. In order to be able to assess the long-term action of the substances, the plants were placed in a greenhouse for 7 days after the spray coating had dried on. Only then were the leaves inoculated with an aqueous zoospore suspension of *Plasmopara viticola*. The vines were then placed initially for 48 hours in a water vapor-saturated chamber at 24° C.

and then for 5 days in a greenhouse at from 20 to 30° C. After this time, to accelerate sporangiophore escape the plants were once again placed for 16 hours in a humid chamber. The extent of the fungal development on the bottoms of the leaves was then determined visually.

The visually determined values for the percentage of affected leaf area were converted into efficiencies as % of the untreated control. Efficiency 0 is the same attack as in the untreated control, efficiency 100 is 0% attack. The efficiencies to be expected for active compound combinations were determined according to the Colby formula (Colby, S. R. (Calculating synergistic and antagonistic responses of herbicide Combinations", Weeds, 15, pp.20–22, 1967) and compared with the observed efficiencies.

TABLE 4

| Ex. | Active compound | Active compound concentration in the spray liquor in ppm | Efficiency in % of the untreated control |
|---|---|---|---|
| 10v | Control (untreated) | (75% attack) | 0 |
| 11v | Compound No. I.32 from Tab. 1 = A | 1.25<br>0.08 | 87<br>73 |
| 12v | Compound No. I.38 Tab. 1 = B | 1.25<br>0.08 | 83<br>47 |
| 13v | IIa = Dimethomorph | 1.25<br>0.08 | 0<br>0 |
| 14v | IIb = Flumetover | 1.25<br>0.08 | 0<br>0 |

TABLE 5

| Ex. | Active compound content in the spray liquor in ppm | Observed efficiency | Calculated efficiency *) |
|---|---|---|---|
| 15 | 1.25A + 1.25IIa | 100 | 87 |
| 16 | 0.08A + 0.08IIa | 93 | 73 |
| 17 | 1.25A + 1.25IIb | 98 | 87 |
| 18 | 0.08A + 0.08IIb | 87 | 73 |
| 19 | 1.25B + 1.25IIa | 100 | 83 |
| 20 | 0.08B + 0.08IIa | 70 | 47 |
| 21 | 1.25B + 1.25IIb | 100 | 83 |
| 22 | 0.08B + 0.08IIb | 68 | 47 |

*) calculated according to the Colby formula

From the results of the experiments it emerges that the observed efficiency at all mixing ratios is higher than the efficiency precalculated according to the Colby formula.

We claim:
1. A fungicidal composition comprising
a) a carbamate I,

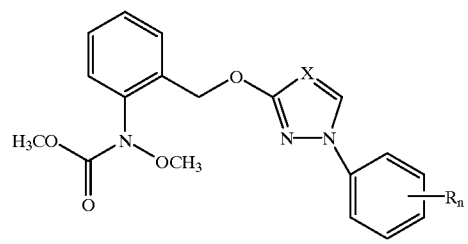

wherein X is CH or N, n is 0, 1 or 2, R is halogen, $C_1$–$C_4$-alkyl or $C_1$–$C_4$-haloalkyl, and the radicals R are identical or different when n is 2, and
b) a carboxamide II selected from the group consisting of the compounds IIa and IIb

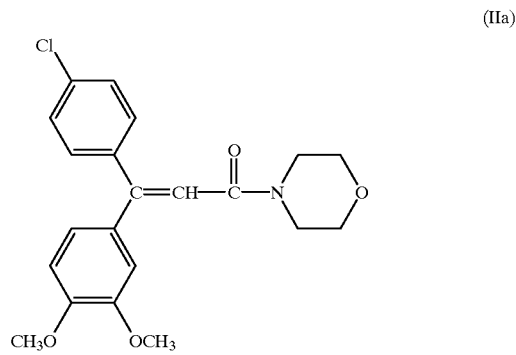

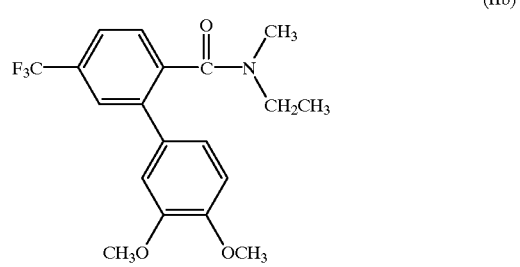

in a synergistically effective amount.
2. The fungicidal composition defined in claim 1, comprising the compound IIa.
3. The fungicidal composition defined in claim 1, comprising the compound IIb.
4. The fungicidal composition defined in claim 1, wherein the weight ratio of the carbamate I to the carboxamide II is from 20:1 to 0.1:2.
5. The composition defined in claim 1, wherein $R_n$ denotes 4-methyl, 4-chloro or 2,4-dichloro.
6. The composition defined in claim 2, wherein $R_n$ denotes 4-methyl, 4-chloro or 2,4-dichloro.
7. The composition defined in claim 3, wherein $R_n$ denotes 4-methyl, 4-chloro or 2,4-dichloro.
8. A method of controlling harmful fungi, which comprises treating the harmful fungi, their habitat or plants, seeds, soils, surfaces, materials or spaces to be kept free from said fungi with synergistically effective amounts of the carbamate I defined in claim 1 and the carboxamide II defined in claim 1.

9. The method of claim 8, wherein the carbamate I and the carboxamide II are applied together or separately at the same time or in succession.

10. The method of claim 8, wherein from 0.01 to 0.5 kg/ha of the carbamate I are applied.

11. The method of claim 8, wherein from 0.05 to 1 kg/ha of the carboxamide II are applied.

12. The method of claim 8, wherein $R_n$ denotes 4-methyl, 4-chloro or 2,4-dichloro.

13. The method of claim 8, wherein the carboxamide II is the compound IIa.

14. The method of claim 8, wherein the carboxamide II is the compound IIb.

15. The method of claim 10, wherein $R_n$ denotes 4-methyl, 4-chloro or 2,4-dichloro.

16. The method of claim 11, wherein $R_n$ denotes 4-methyl, 4-chloro or 2,4-dichloro.

\* \* \* \* \*